US012788452B2

(12) United States Patent
Murdoch et al.

(10) Patent No.: US 12,788,452 B2
(45) **Date of Patent: *Nov. 10, 2026**

(54) KYPHOPLASTY SYSTEM AND METHOD

(71) Applicant: Osteon Medical LLC, Grand Island, NE (US)

(72) Inventors: Nathan William Murdoch, Grand Island, NE (US); Cody L. Evans, Grand Island, NE (US)

(73) Assignee: Osteon Medical LLC, Grand Island, NE (US)

(*) Notice: Subject to any disclaimer, the term of this patent is extended or adjusted under 35 U.S.C. 154(b) by 0 days.

This patent is subject to a terminal disclaimer.

(21) Appl. No.: 19/080,164

(22) Filed: Mar. 14, 2025

(65) Prior Publication Data

US 2025/0241690 A1 Jul. 31, 2025

Related U.S. Application Data

(63) Continuation of application No. 18/237,722, filed on Aug. 24, 2023, now Pat. No. 12,274,478, which is a (Continued)

(51) Int. Cl.

*A61B 17/88* (2006.01)
*A61B 17/70* (2006.01)

(Continued)

(52) U.S. Cl.

CPC ...... *A61B 17/7097* (2013.01); *A61B 17/8805* (2013.01); *A61B 2017/564* (2013.01);

(Continued)

(58) Field of Classification Search

CPC . A61B 17/88; A61B 17/8802; A61B 17/8805; A61B 17/8811; A61B 17/8819;

(Continued)

(56) References Cited

U.S. PATENT DOCUMENTS 4,405,249 A 9/1983 Scales
5,571,189 A 11/1996 Kuslich et al.

(Continued)

FOREIGN PATENT DOCUMENTS

EP 3470000 A1 4/2019

OTHER PUBLICATIONS

Cornelis et al., "Innovative spine implants for improved augmentation and stability in neoplastic vertebral compression fracture," Medicina, Aug. 2019, 55(8):426.

(Continued)

*Primary Examiner* — Anu Ramana

(74) *Attorney, Agent, or Firm* — Fish & Richardson P.C.

(57) ABSTRACT

A kyphoplasty system disclosed herein includes various instruments which can be selectively used to perform a kyphoplasty operation on a patient. For example, in some embodiments the kyphoplasty system includes an inflation plunger that is used to deliver a balloon inflation medium to enlarge an implantable balloon device. Further, some embodiments described herein include a connection system between the implantable balloon device and its delivery shaft that is simple to construct and easy to use. For example, in some embodiments one or more sutures are used to releasably connect the implantable balloon device to its delivery shaft.

19 Claims, 10 Drawing Sheets

Related U.S. Application Data continuation of application No. 17/406,406, filed on Aug. 19, 2021, now Pat. No. 11,771,479, which is a continuation of application No. 17/157,165, filed on Jan. 25, 2021, now Pat. No. 11,103,290.

(51) Int. Cl.
*A61B 17/56* (2006.01)
*A61M 25/10* (2013.01)

(52) U.S. Cl.
CPC . *A61M 25/10182* (2013.11); *A61M 25/10186* (2013.11); *A61M 2025/1079* (2013.01)

(58) Field of Classification Search
CPC ............ A61B 17/8822; A61B 17/8825; A61B 17/885; A61B 17/8855; A61B 17/8858
See application file for complete search history.

(56) References Cited

U.S. PATENT DOCUMENTS

| | | | | |
|---|---|---|---|---|
| 5,954,728 | A | 9/1999 | Heller | |
| 6,042,380 | A | 3/2000 | Rowe | |
| 6,080,801 | A * | 6/2000 | Draenert | A61L 24/0073 523/205 |
| 6,127,597 | A | 10/2000 | Beyar et al. | |
| 6,395,007 | B1 | 5/2002 | Bhatnagar et al. | |
| 6,561,724 | B1 | 5/2003 | Carletti | |
| 6,716,216 | B1 | 4/2004 | Boucher | |
| 6,730,095 | B2 | 5/2004 | Olson, Jr. | |
| 6,875,212 | B2 | 4/2005 | Shaolian | |
| 7,556,650 | B2 | 7/2009 | Collins et al. | |
| 7,628,800 | B2 | 12/2009 | Sherman et al. | |
| 7,666,205 | B2 | 2/2010 | Weikel et al. | |
| 8,038,682 | B2 | 10/2011 | McGill et al. | |
| 8,092,464 | B2 | 1/2012 | McKay | |
| 8,308,693 | B2 | 11/2012 | Miller | |
| 8,491,591 | B2 | 7/2013 | Furderer | |
| 8,647,378 | B2 | 2/2014 | Mews et al. | |
| 8,708,955 | B2 * | 4/2014 | Tilson | A61B 17/8855 604/103.1 |
| 8,827,981 | B2 * | 9/2014 | Liu | A61B 17/8827 604/95.04 |
| 8,870,888 | B2 | 10/2014 | Steffen et al. | |
| 8,900,304 | B1 | 12/2014 | Alobaid | |
| 8,986,386 | B2 | 3/2015 | Oglaza et al. | |
| 9,101,408 | B1 * | 8/2015 | Dix | A61B 17/00234 |
| 9,283,018 | B1 | 3/2016 | Alobaid | |
| 9,308,361 | B2 | 4/2016 | Muni | |
| 9,358,058 | B2 | 6/2016 | O'Halloran et al. | |
| 9,414,933 | B2 | 8/2016 | Banouskou | |
| 9,579,130 | B2 | 2/2017 | Oglaza et al. | |
| 10,820,933 | B1 | 11/2020 | Murdoch et al. | |
| 10,821,002 | B1 | 11/2020 | Hibri | |
| 10,881,522 | B2 | 1/2021 | Hibri | |
| 11,103,290 | B1 | 8/2021 | Murdoch et al. | |
| 11,246,633 | B1 | 2/2022 | Murdoch et al. | |
| 11,351,039 | B2 * | 6/2022 | Milella, Jr. | A61F 2/447 |
| 11,697,005 | B2 * | 7/2023 | Tilson | A61B 17/8827 606/191 |
| 11,771,479 | B2 | 10/2023 | Murdoch et al. | |
| 11,903,628 | B1 | 2/2024 | Murdoch | |
| 12,274,478 | B2 | 4/2025 | Murdoch et al. | |
| 2002/0049448 | A1 | 4/2002 | Sand et al. | |
| 2005/0245938 | A1 | 11/2005 | Kochan | |
| 2006/0079905 | A1 | 4/2006 | Beyar | |
| 2006/0100706 | A1 | 5/2006 | Shadduck et al. | |
| 2007/0293866 | A1 | 12/2007 | Stoeckel et al. | |
| 2010/0069912 | A1 | 3/2010 | McCormack | |
| 2010/0198225 | A1 | 8/2010 | Thompson et al. | |
| 2010/0249933 | A1 | 9/2010 | Trieu | |
| 2010/0284734 | A1 | 11/2010 | Turnour | |
| 2015/0012002 | A1 | 1/2015 | Steffen et al. | |
| 2017/0252077 | A1 | 9/2017 | DiPoto et al. | |
| 2018/0256188 | A1 | 9/2018 | Goshayeshgar | |
| 2019/0167333 | A1 | 6/2019 | Druma | |
| 2021/0015531 | A1 | 1/2021 | Murdoch et al. | |
| 2021/0015532 | A1 | 1/2021 | Murdoch et al. | |
| 2021/0015533 | A1 | 1/2021 | Murdoch et al. | |
| 2021/0015534 | A1 | 1/2021 | Murdoch et al. | |
| 2022/0233219 | A1 | 7/2022 | Murdoch et al. | |
| 2024/0081877 | A1 | 3/2024 | Murdoch et al. | |

OTHER PUBLICATIONS

DePuy Synthes, "VBS-Vertebral Body Stenting System: Surgical Technique," from URL <http://synthes.vo.llnwd.net/o16/LLNWMB8/INT%20Mobile/Synthes%20International/SGT-EMEA-Agile/SE_818940AA/SE_818940AAeng.pdf>, Nov. 2020, 27 pages.
izimed.com, "Kiva VCF Treatment System: The Implant Solution for Restoration of Sagittal Alignment," from URL <https://static1.squarespace.com/static/5cba31329b8fe86db05fc0eb/t/5d922d0d7ee00f102eb54317/1569860889779/L127+KIVA+Surgeon+Brochure%2C+Rev.+B.pdf>, Sep. 9, 2019, 8 pages.
PCT International Search Report and Written Opinion in International Appln. No. PCT/US2022/013281, May 19, 2022, 16 pages.

* cited by examiner

SECTION A-A

SECTION H-H

SECTION F-F

KYPHOPLASTY SYSTEM AND METHOD

CROSS-REFERENCE TO RELATED APPLICATIONS

This application is a continuation application of U.S. application Ser. No. 18/237,722, filed on Aug. 24, 2023 (now U.S. Pat. No. 12,274,478), which is a continuation of U.S. application Ser. No. 17/406,406, filed on Aug. 19, 2021 (now U.S. Pat. No. 11,771,479), which is a continuation of U.S. application Ser. No. 17/157,165, filed on Jan. 25, 2021 (now U.S. Pat. No. 11,103,290), the entire contents of which are hereby incorporated by reference.

TECHNICAL FIELD

This document generally relates to kyphoplasty and/or other interventional spinal procedures.

BACKGROUND

Kyphoplasty is a minimally invasive surgical procedure for treatment of pain caused by vertebral body compression fractures. Typically, the procedure involves insertion of one or more coaxial 8-10 gauge bone introducer needles under fluoroscopic guidance into one or more fractured vertebral bodies utilizing a bipedicular, unipedicular, or extrapedicular approach. In some approaches, after a bone introducer needle is in place, the inner portion of the bone introducer needle is removed and the outer portion of the bone introducer needle remains as a guide and support for the remaining procedure. Through the bone introducer needle, a drill and curette are utilized for cavity creation in the vertebral body. In many cases, after the cavity is created, the drill and curette are removed, and a deflated balloon is inserted into the cavity of the vertebral body. The balloon is then inflated, for example, by injecting a solution into the balloon, thereby expanding the drilled cavity into a desired size within the vertebral body. When the cavity is expanded to the desired size, the balloon is deflated and removed from the vertebral body. Usually in such cases, a bone filler is advanced into the vertebral body, and the expanded cavity is filled with cement.

SUMMARY

Some embodiments described herein include a kyphoplasty system. The kyphoplasty system includes a multi-functional device that simplifies cavity creation and filling processes, with improved height restoration of a fractured vertebral body. For example, the kyphoplasty system can be configured to maintain a desired anatomic height (e.g., after a balloon is inserted to expand a vertebral body cavity to a desired height) before and during the delivery of cement to the expanded cavity. Further, in some examples described herein, the kyphoplasty system can employ an instrument that is configured to both expand the vertebral body cavity to the desired anatomic height (e.g., using a balloon) and also fill the vertebral body cavity with cement.

Embodiments of the multi-functional device disclosed herein integrate a balloon device with a bone filler device. Some such embodiments are configured as a single unit which can be detachably coupled to a distal end of an elongated shaft of a kyphoplasty device. The multi-functional device can be introduced into a fractured vertebral body by advancing the shaft of the kyphoplasty device, with the multi-functional device coupled at the distal end, into the fractured vertebral body. The shaft with the multi-functional device can be inserted into the vertebral body cavity of a fractured vertebral body through, for example, a bone introducer needle or sheath. While inserted into the vertebral body cavity, the multi-functional device then advantageously allows both inflating the balloon and injecting bone filling substance into the fractured vertebral body cavity. Such balloon inflation and bone filler injection can be performed sequentially, simultaneously, or alternatingly while the multi-functional device remains in the vertebral body cavity.

The balloon can be configured to form various inflated shapes, such as spheres, cylinders, cubes, diamonds, prisms, and other multifaceted 3-D shapes. For example, multifaceted shapes, such as diamond shapes, can increase surface area contact. In addition or alternatively, the kyphoplasty systems described herein can include multiple sets of shafts and dual port devices that are operated simultaneously or in sequence.

Some embodiments of the technologies described herein include a connection system that allows compact, easy, and reliable engagement between instruments in the kyphoplasty system or other interventional procedures. For example, the connection system can be sized sufficiently small and provide minimum interference between different sets of instruments that are arranged together in a dense area where many instruments are introduced into the patient. That way, multiple instruments may be used in a small area of the patient body at the same time while also reducing obstructions in the working space located exterior to the patient. For example, the kyphoplasty system in some embodiments herein may use a plurality of bone introducer needles to access a plurality of vertebral bodies that are closely arranged, and each bone introducer needle may include a needle (e.g., a cannula) and a head (e.g., an inner connector) fixed to an end of the needle. Preferably, the head of the bone introducer needle and/or each exterior connector are sized sufficiently small and provide minimum interference between different sets of instruments that are arranged together in a dense area where many instruments are introduced into the patient.

Some embodiments of the technologies described herein include an introducer needle with a backflow prevention device. Embodiments of the backflow prevention device of the introducer needle include a one-way valve arranged in a hub of the introducer needle. For example, the introducer needle includes a needle and a hub mounted at an end of the needle. The hub defines an interior space being in fluid communication with a canal of the needle, and further includes a one-way valve arranged within the interior space and configured to prevent backflow of blood or body fluids (e.g., flow in a direction away from a patient's body) when, for example, a biopsy needle is removed from the patient's body through the introducer needle. In addition, the hub can provides a coupling mechanism (e.g., a luer lock) for an instrument (e.g., a coaxial biopsy device).

In a first aspect, this disclosure is directed to a kyphoplasty system that includes a balloon device and an inflation plunger. The balloon device defines a first lumen and includes a balloon implant member comprising a balloon mounted on a balloon shaft. The balloon device also includes a balloon member delivery shaft. The balloon implant member is releasably attached to a distal end portion of the balloon member delivery shaft. The inflation plunger defines a second lumen. The inflation plunger is configured to slidingly engage in the first lumen and to convey, via the second lumen, an inflation medium to inflate the balloon.

Such a kyphoplasty system may optionally include one or more of the following features. A distal end portion of the inflation plunger may define one or more inflation apertures that allow the inflation medium to exit the second lumen. The distal end portion of the inflation plunger may include a first seal located proximal of the one or more inflation apertures. The distal end portion of the inflation plunger may include a second seal located distal of the one or more inflation apertures. The first and second seals may seal against a wall of the first lumen. The balloon implant member may also include one or more one-way valves arranged to allow flow of the inflation medium to inflate the balloon and to prevent the inflation medium from exiting the balloon. In some embodiments, the one or more one-way valves includes at least one of a one-way flap valve or a one-way sleeve valve. The balloon implant member may be releasably attached to the distal end portion of the balloon member delivery shaft by one or more sutures. In some embodiments, the one or more sutures includes two sutures that are each looped through a respective opening of two openings defined by the balloon shaft.

In another aspect, this disclosure is directed to a method for performing a kyphoplasty procedure. The method includes: inserting a balloon implant member comprising a balloon mounted on a balloon shaft into a vertebral body cavity and inflating the balloon. The balloon implant member may be releasably attached to a distal end portion of a balloon member delivery shaft such that a lumen defined by the balloon member delivery shaft and a lumen defined by the balloon shaft adjoin to define a first lumen. The inflating the balloon is performed by injecting an inflation medium into a second lumen defined by an inflation plunger that is within the first lumen.

Such a method for performing a kyphoplasty procedure may optionally include one or more of the following optional features. The method may also include, prior to inserting the balloon implant member into the vertebral body cavity, advancing a bone introducer needle adjacent to the vertebral body cavity. The balloon implant member may be inserted into the vertebral body cavity through the bone introducer needle. The method may also include, after advancing the bone introducer needle adjacent to the vertebral body cavity and before inserting the balloon implant member into the vertebral body cavity, advancing a space-making balloon through the bone introducer needle and inflating the space-making balloon within the vertebral body cavity. The method may also include, after inflating the balloon, retracting the inflation plunger from the first lumen. The method may also include, after retracting the inflation plunger from the first lumen, injecting filler material into the vertebral body cavity external to the balloon implant member. In some embodiments, the filler material is injected into the vertebral body cavity external to the balloon implant member via the first lumen. In particular embodiments, the filler material is injected into the vertebral body cavity external to the balloon implant member via an elongate needle within the first lumen. The method may also include, after inflating the balloon, detaching the balloon implant member from the balloon member delivery shaft such that the balloon implant member remains in the vertebral body cavity. The detaching may include removing one or more sutures by which the balloon implant member is releasably attached to the distal end portion of the balloon member delivery shaft during the inserting.

The apparatuses, systems, devices, and techniques described herein may provide one or more of the following advantages. Some embodiments described herein include a kyphoplasty system that includes a multi-functional device providing both balloon inflation and bone filling functionalities together in a single unit, thereby simplifying a kyphoplasty procedure. The dual port device improves height restoration of a fractured vertebral body by the balloon inflation, and permits for the vertebral body cavity to be filled with the bone filler without losing the restored height.

Further, some embodiments described herein include a connection system between the implantable balloon device and its delivery shaft that is simple to construct and easy to use. For example, in some embodiments one or more sutures are used to releasably connect the implantable balloon device to its delivery shaft. The one or more sutures are advantageously low-profile, as well as easy and intuitive to use. That is, clinicians can easily detach the implantable balloon device from its delivery shaft by withdrawing the one or more sutures from engagement with the implantable balloon device.

Moreover, some embodiments described herein include an inflation plunger that is used to deliver a balloon inflation medium to enlarge the implantable balloon device. As described further below, the design and functionality of the inflation plunger advantageously allows for a compact and concise overall design of the kyphoplasty systems described herein.

The details of one or more implementations are set forth in the accompanying drawings and the description below. Other features and advantages will be apparent from the description and drawings, and from the claims.

DETAILED DESCRIPTION OF ILLUSTRATIVE EMBODIMENTS

Figure 1:
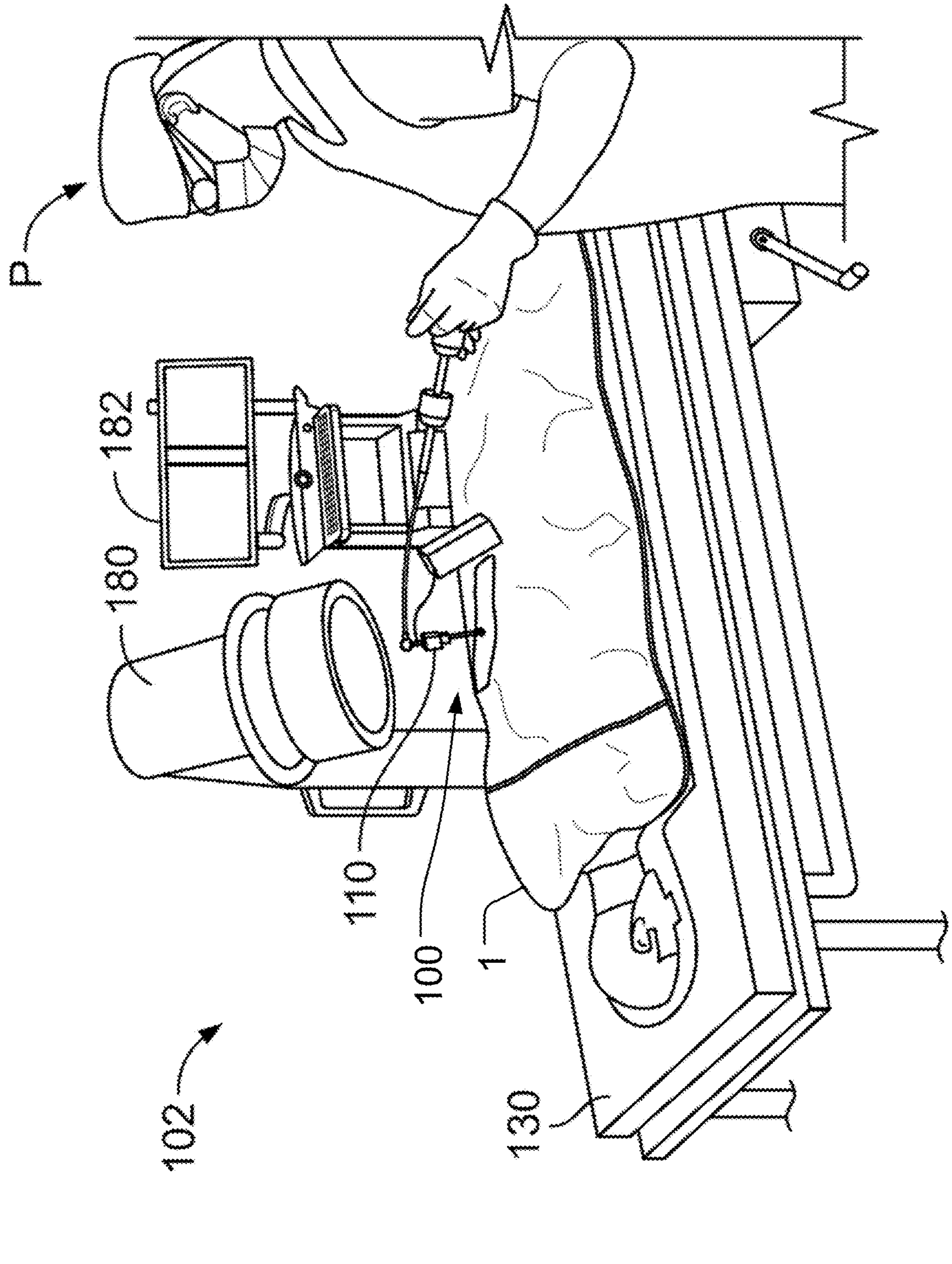
FIG. 1 depicts the clinical use of an example kyphoplasty system that is being used to restore a fractured vertebral body.

FIG. 1 illustrates an example kyphoplasty system 100 being used by a practitioner P to perform a kyphoplasty procedure in a surgical theater 102. The patient 1 is laying prone on a prone table mat 130 during the kyphoplasty procedure.

In the surgical theater 102, the kyphoplasty system 100 can be used in conjunction with an image scanner 180, such as a C-arm fluoroscopy machine, and a display device 182 configured to receive images (e.g., still and/or video images) from the image scanner 180 and to display the images to assist a practitioner P with visualization during the kyphoplasty procedure. In some embodiments, one or more components of the kyphoplasty system 100 can include one or more radiopaque markers. For example, in some embodiments the kyphoplasty system 100 includes an implantable balloon member that can include one or more radiopaque markers.

While the kyphoplasty system 100 and procedure is described in greater detail below, briefly the kyphoplasty procedure includes advancing a bone introducer needle toward a vertebral body of the patient 1. While the bone introducer needle is in place, the inner portion of the bone introducer needle is removed and the outer portion of the bone introducer needle remains as a guide and support for the remaining procedural steps.

Through the bone introducer needle, a drill and curette are utilized for cavity creation in the vertebral body. In many cases, after the cavity is created, the drill and curette are removed, and a deflated balloon is inserted into the cavity of the vertebral body. The balloon is then inflated, for example, by injecting a solution or filler material (e.g., bone cement) into the balloon, thereby expanding the drilled cavity into a desired size within the vertebral body and thereby restoring the height of the vertebral body. When the vertebral body cavity is expanded to the desired size by the inflated balloon, a bone filler (e.g., bone cement) is injected into the vertebral body cavity space that is external to the balloon. When the expanded cavity is sufficiently filled with the bone filler material, the balloon is then detached and left within the restored vertebral body, and the other components of the kyphoplasty system 100 are retracted from the patient 1.

Figure 2:
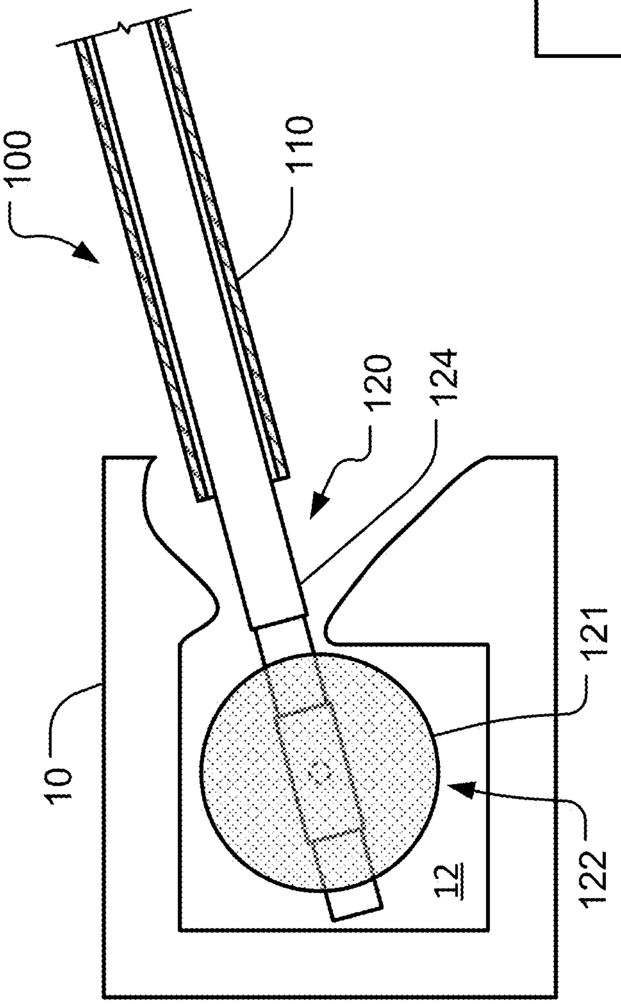
FIG. 2 schematically illustrates the implantation of an example kyphoplasty apparatus to restore a fractured vertebral body.

FIG. 2 schematically illustrates a distal end portion of the kyphoplasty system 100 partially within a vertebral body 10, as per the kyphoplasty procedures described herein. The kyphoplasty system 100 includes a balloon device 120 that is advanced into a body cavity 12 of the vertebral body 10 via an introducer needle 110 (shown in longitudinal cross-section).

The balloon device 120 includes an expandable balloon implant member 122 which is positioned within the vertebral body cavity 12. The balloon implant member 122 is releasable attached to a balloon member delivery shaft 124. As described further below, a lumen of the balloon member delivery shaft 124 is used to deliver bone filler material (e.g., bone cement) into the expandable balloon implant member 122 and into the vertebral body cavity 12 external to the expanded balloon implant member 122.

Figure 3:
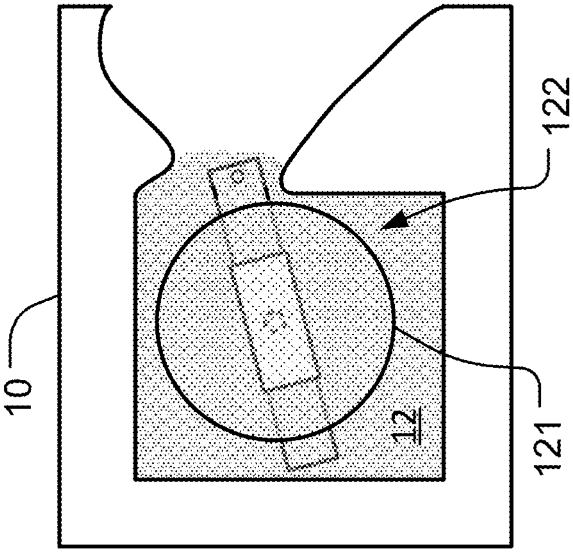
FIG. 3 schematically illustrates the vertebral body of FIG. 2 after restoration using the kyphoplasty systems described herein.

As schematically depicted in FIG. 3, after the bone filler material is injected into the expandable balloon implant member 122 and into the vertebral body cavity 12, the balloon member delivery shaft 124 is then detached from the balloon implant member 122. The balloon implant member 122 is left implanted within the restored vertebral body cavity 12 of the vertebral body 10. While in the depicted scenario a single balloon implant member 122 is implanted within the restored vertebral body cavity 12, in some cases two balloon implant members 122 are implanted within the restored vertebral body cavity 12.

This ends the brief summary description of the kyphoplasty procedures and systems disclosed herein. Additional details regarding the kyphoplasty system 100 and the kyphoplasty procedures performed using the kyphoplasty system 100 will now be provided in reference to FIGS. 4-16.

Figure 4:
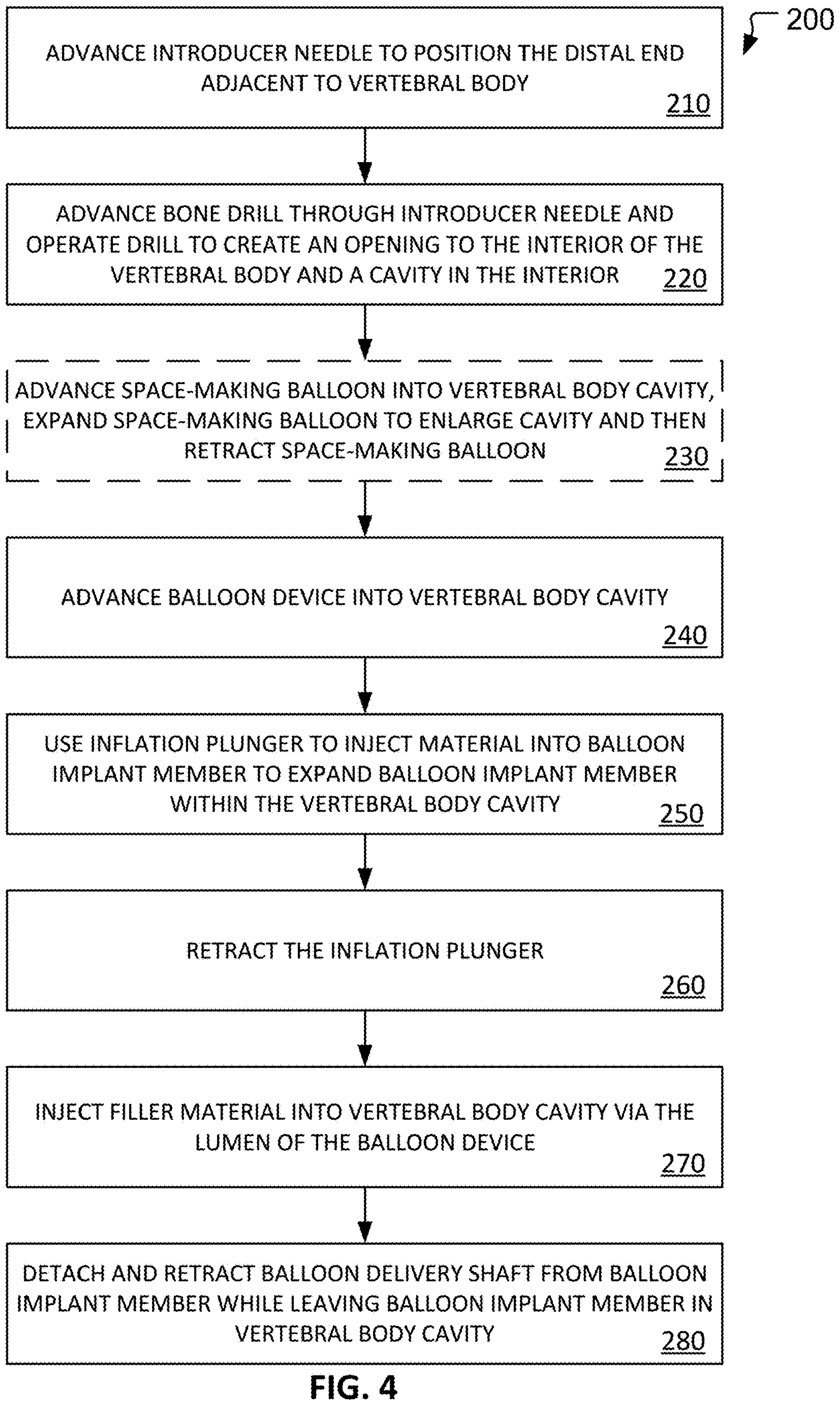
FIG. 4 is a flowchart that describes an example kyphoplasty method in accordance with some embodiments.

FIG. 4 provides a flowchart of an example balloon kyphoplasty procedure 200. The kyphoplasty procedure 200 utilizes the kyphoplasty systems 100 described herein to treat a fractured vertebra.

In step 210, a bone introducer needle (which can also be referred to as a sheath or trocar) is advanced toward the fractured vertebra of the patient under x-ray fluoroscopy guidance. The bone introducer needle defines a lumen through which various instruments of the kyphoplasty system 100, as described further below, can be advanced to treat the fractured vertebral body of the patient. In some embodiments, the introducer needle includes a backflow prevention device configured to prevent backflow of blood or body fluids through the needle.

In step 220, a bone drill is advanced through the lumen of the introducer needle toward the fractured vertebral body. The bone drill is then rotatably driven to create an opening to access the vertebral body cavity. Afterwards, in some cases the introducer needle is then advanced farther, through the opening created by the bone drill. The bone drill can also be used to create an initial open void inside of the vertebral body. The bone drill can then be retracted and removed from the lumen of the introducer needle.

In optional step 230, a high-pressure space-making balloon can be advanced through the lumen of the introducer needle and into the vertebral body cavity. In some cases, the high-pressure space-making balloon can be an 800 psi balloon, a 1000 psi balloon, a 1200 psi balloon, and the like, without limitation. The space-making balloon can then be inflated. The inflation of the space-making balloon elevates the fractured vertebra to its pre-fracture height, and creates a larger void in the vertebral body cavity. The space-making balloon can then be deflated. Then, the space-making balloon can be retracted and removed from the lumen of the introducer needle.

In step 240, a balloon device of the kyphoplasty systems 100 described herein can be advanced through the lumen of the balloon device introducer needle and into the vertebral body cavity. The balloon member of the balloon device is deflated and configured in a low-profile delivery configuration during this step.

Figure 5:
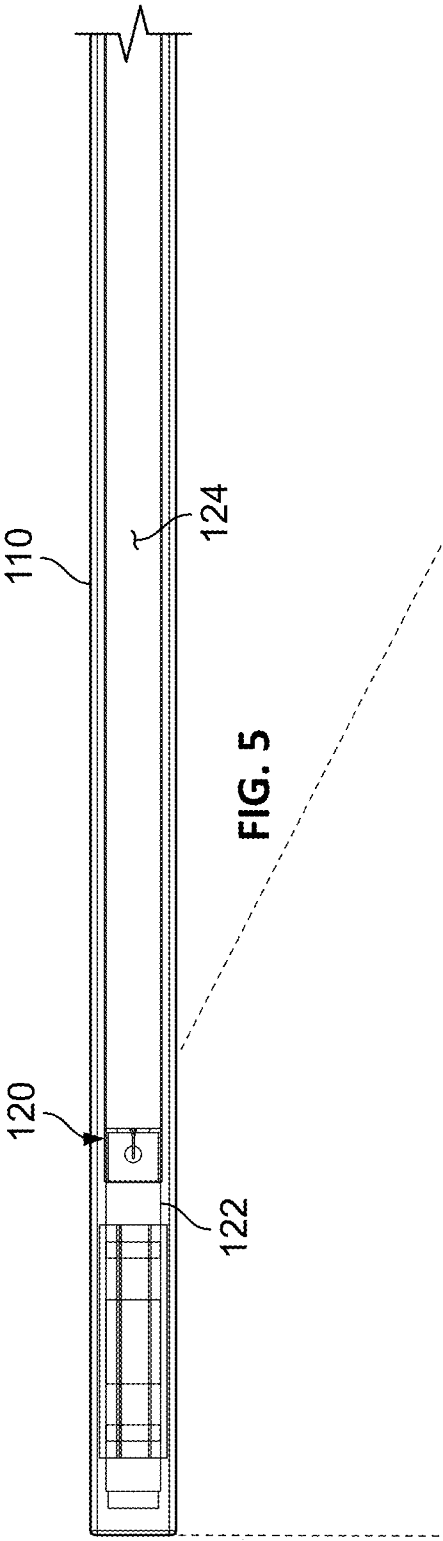
FIG. 5 illustrates an example kyphoplasty system in a delivery configuration.
Figure 6:
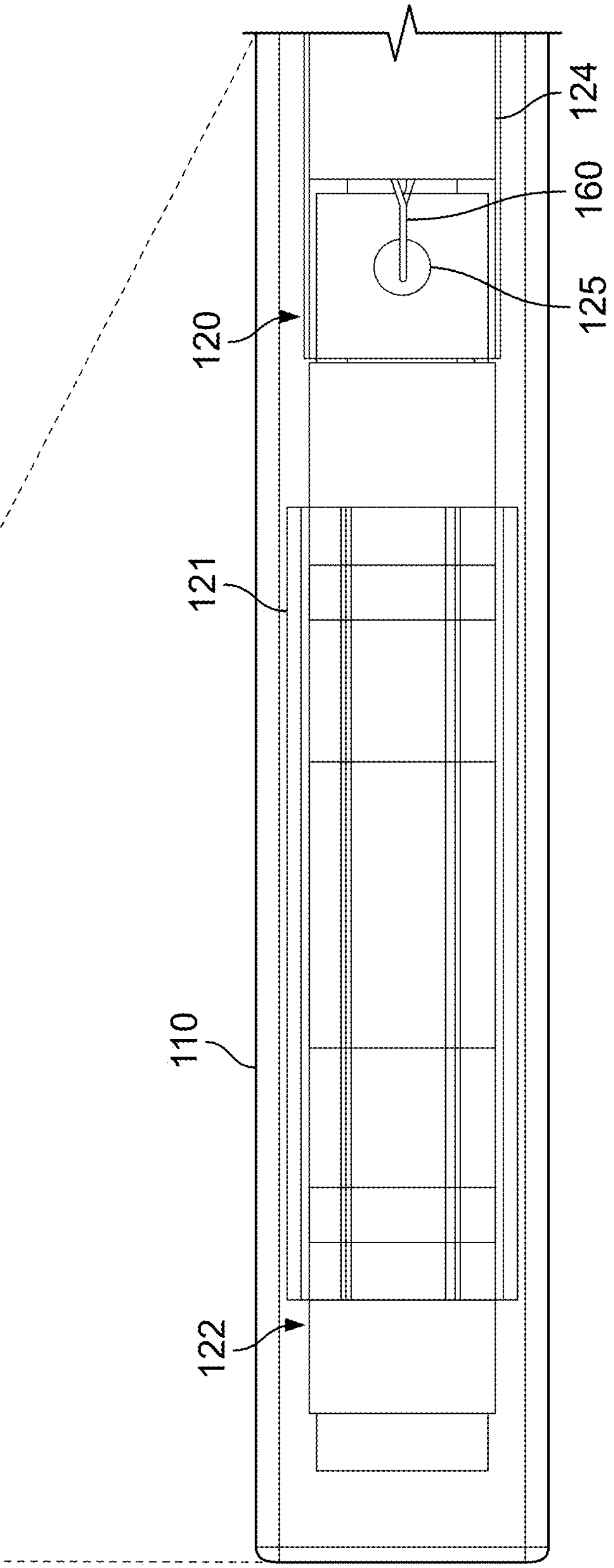
FIG. 6 is a close-up view of a distal end portion of the kyphoplasty system of FIG. 5.

FIGS. 5 and 6 depict an example balloon device 120 of the kyphoplasty systems 100 described herein. The balloon device 120 is deflated and configured in a low-profile delivery configuration, and is positioned within the lumen of an introducer needle 110 (shown transparently). The balloon device 120 includes a balloon implant member 122 and a balloon member delivery shaft 124. The balloon implant member 122 is releasably coupled to a distal end portion of the balloon member delivery shaft 124. As described further below, one or more removable sutures 160 (FIG. 6) can be used to releasably couple the balloon implant member 122 to the balloon member delivery shaft 124.

The balloon implant member 122 and the balloon member delivery shaft 124 each define a lumen. While the balloon implant member 122 is releasably coupled to the balloon member delivery shaft 124, the lumens of the balloon implant member 122 and the balloon member delivery shaft 124 are adjoining so as to function as a single lumen.

Still referring to FIG. 4, in step 250 an inflation plunger that is positioned in the lumens of the balloon implant member 122 and the balloon member delivery shaft 124 is used to inflate the balloon implant member 122. This inflation of the balloon implant member 122 is executed while the balloon implant member 122 is located in the vertebral body cavity.

Figure 7:
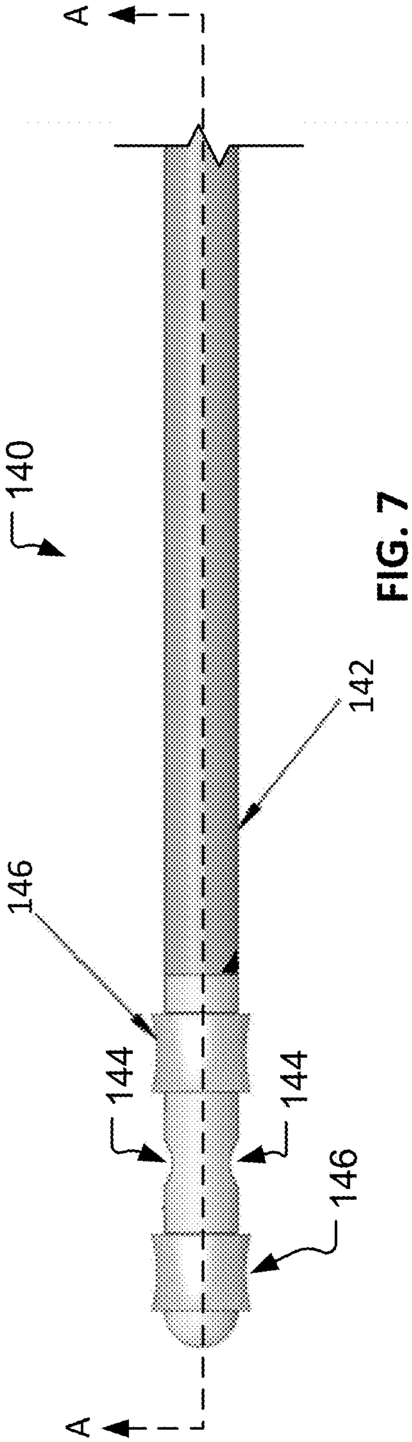
FIG. 7 illustrates an example inflation plunger component of the kyphoplasty systems described herein.
Figure 8:
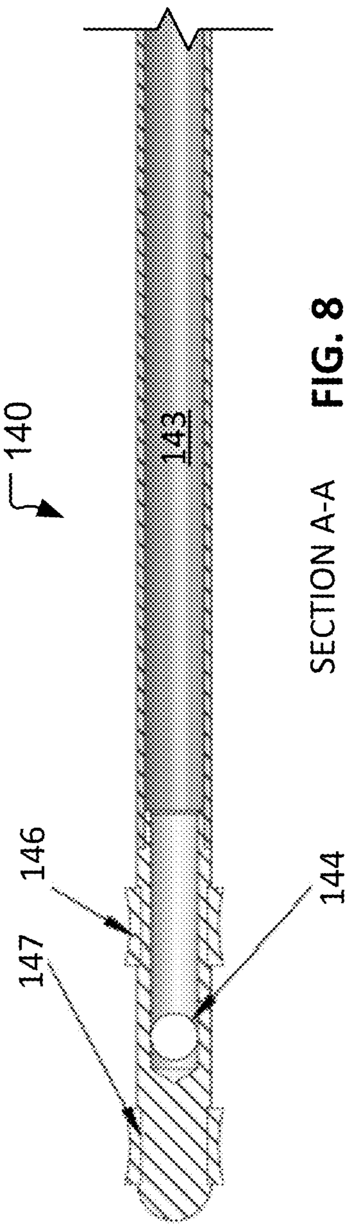
FIG. 8 is a longitudinal cross-section view of the inflation plunger of FIG. 7.

FIGS. 7 and 8 depict an example inflation plunger 140 of the kyphoplasty systems 100 described herein. The inflation plunger 140 includes a shaft 142 that defines a lumen 143. A distal end portion of the shaft 142 defines one or more inflation apertures 144. The inflation apertures 144 are openings to the lumen 143. In this example, two inflation apertures 144 are included in the inflation plunger 140.

Two or more seals 146 are coupled to the distal end portion of the shaft 142. In the depicted example, two seals 146 are included. In some embodiments, the seals 146 can be made of an elastomeric material such as, but not limited to, silicone or urethane. In some embodiments, each seal of the seals 146 is seated in a complementary groove 147 defined by the outer diameter of the distal end portion of the shaft 142.

The inflation apertures 144 are positioned between the seals 146. That is, a first seal of the two or more seals 146 is located proximal of the inflation apertures 144, and a second seal of the two or more seals 146 is located distal of the inflation apertures 144.

As stated above, the inflation plunger 140 is advanced through the lumens of the balloon implant member 122 and the balloon member delivery shaft 124.

Figure 9:
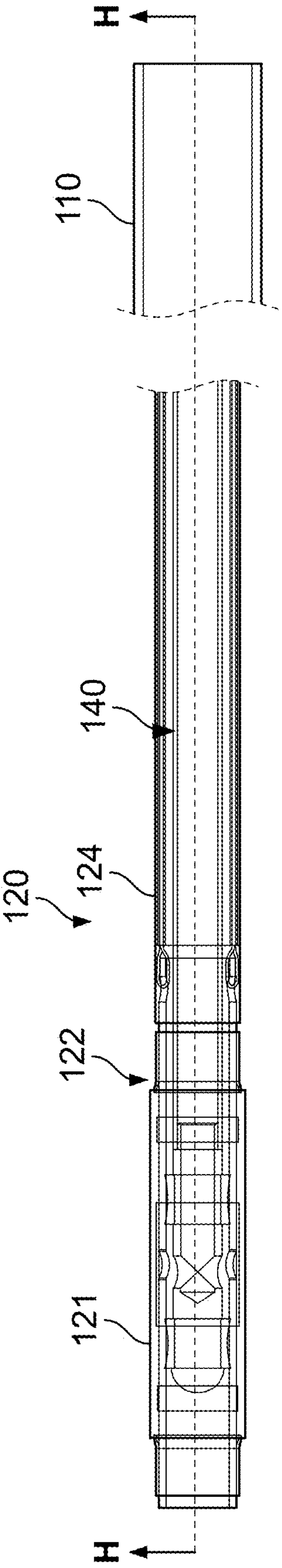
FIG. 9 illustrates the kyphoplasty system of FIG. 5 with the balloon member in an expanded configuration.
Figure 10:
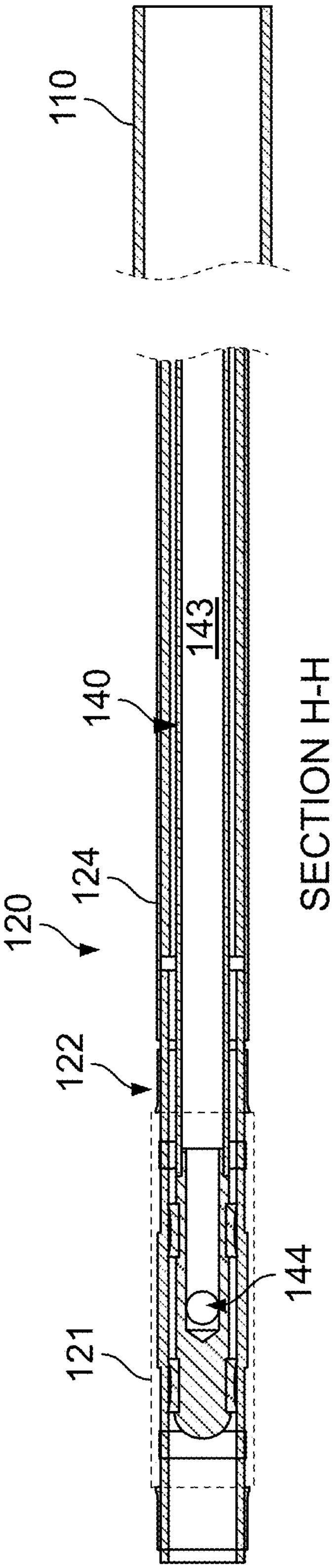
FIG. 10 is a longitudinal cross-section view of the kyphoplasty system of FIG. 9.

FIGS. 9 and 10 depict the inflation plunger 140 within the lumens of the balloon implant member 122 and the balloon member delivery shaft 124. The balloon implant member 122 is still not inflated in this arrangement.

Figure 11:
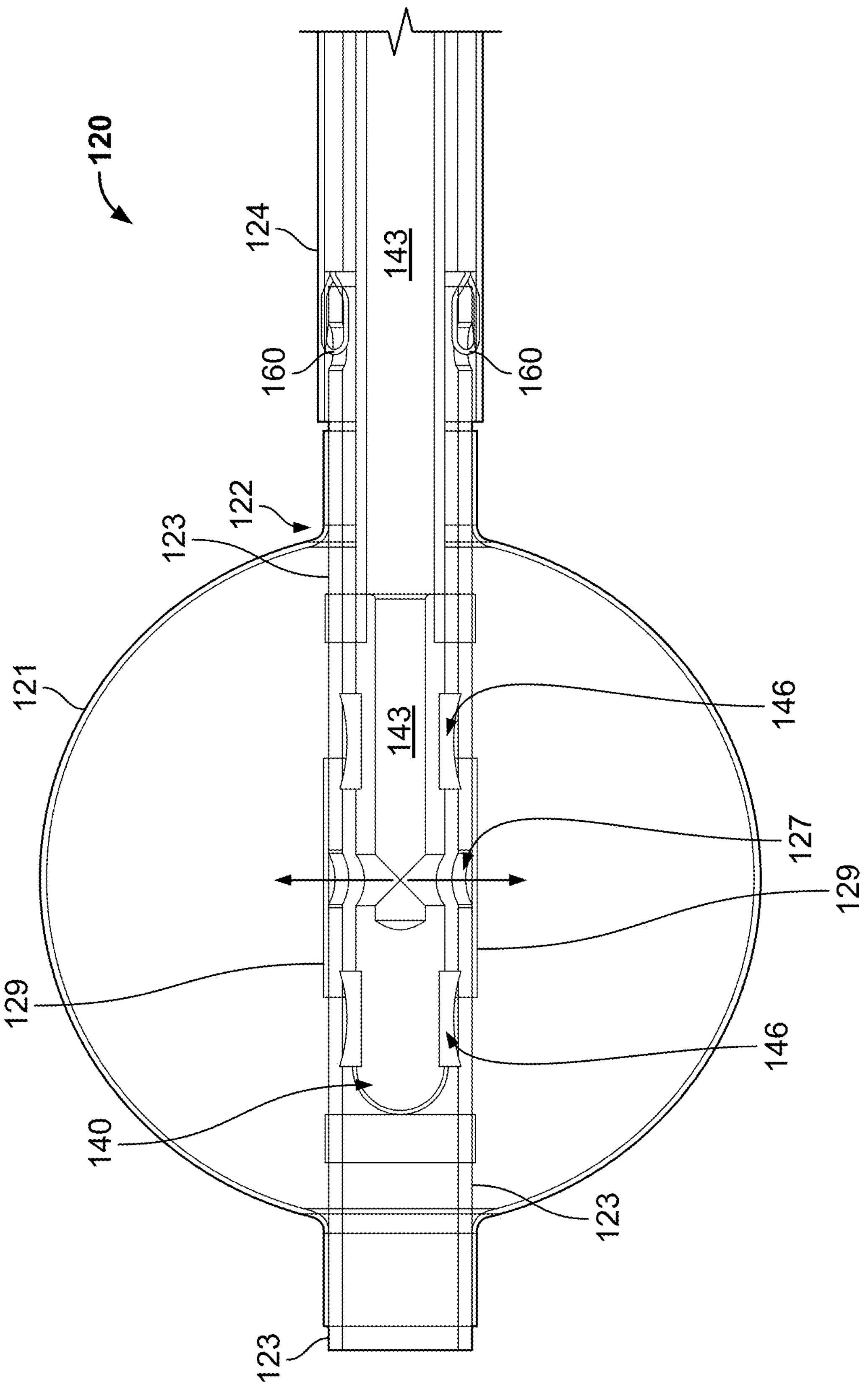
FIG. 11 is a close-up view of the distal end portion of the kyphoplasty system of FIGS. 7 and 8.

FIG. 11 depicts the injection of inflation medium into the balloon implant member 122 using the inflation plunger 140, as per step 250 of the balloon kyphoplasty procedure 200 (FIG. 4). This causes a balloon 121 of the balloon implant member 122 to expand within the vertebral body cavity (see also FIG. 2).

To assist in the understanding of how step 250 takes place, additional information regarding structural details of the balloon implant member 122 will now be explained. The balloon implant member 122 includes the balloon 121 that is fixedly attached to a balloon shaft 123. The balloon shaft 123 defines the lumen of the balloon implant member 122 that is aligned with the lumen of the balloon member delivery shaft 124. The balloon shaft 123 defines one or more apertures 127. The one or more apertures 127 provide fluid communication between the lumen of the balloon implant member 122 and the interior of the balloon 121. Accordingly, inflation medium can pass into the interior of the balloon 121 via the one or more apertures 127 of the balloon shaft 123.

The balloon implant member 122 also includes one or more one-way valves 129. The one or more one-way valves 129 are positioned between the one or more apertures 127 and the interior of the balloon 121. Accordingly, the one or more one-way valves 129 allow flow of the inflation medium into the balloon 121 (to inflate the balloon 121), but prevent the flow of the inflation medium in the opposite direction. This means that the inflation medium that enters the interior of the balloon 121 stays in the interior of the balloon 121. In some embodiments, the one or more one-way valves 129 may be a sleeve made of a flexible material such as, but not limited to, silicone or urethane. Accordingly, the one or more one-way valves 129 may be referred to as sleeve valves. In some embodiments, the one or more one-way valves 129 may include displaceable flap members that open to allow flow into the interior of the balloon 121, and that close when the flow is stopped. Other types of one-way valves 129 can also be utilized.

The inflation medium is injected by the practitioner P (FIG. 1) into the lumen 143 of the inflation plunger 140. In some cases, the balloon 121 is filled to about 200 psi, or in a range from about 150 psi to about 250 psi, without limitation. In some cases, the inflation medium that is injected into the balloon 121 is a type of solidifying liquid such as orthopedic cement or bone cement (e.g., polymethyl methacrylate, calcium phosphate, magnesium phosphate, amorphous magnesium phosphate, etc.). In some cases, a contrast bone cement can be used as the inflation medium that is injected into the balloon 121.

The inflation medium flows distally through the lumen 143 of the inflation plunger 140 and exits the inflation plunger 140 via the one or more apertures 144 (FIGS. 7 and 8).

Still referring to FIG. 11, the two or more seals 146 of the inflation plunger 140 are in contact with the inner wall of the balloon shaft 123. Accordingly, a confined space exists between the outer wall surface of the inflation plunger 140, the inner wall surface of the balloon shaft 123, and between the two or more seals 146. The one or more apertures 144 of the inflation plunger 140 serve as the inlet(s) to the confined space. The one or more apertures 127 of the balloon shaft 123 serve as the outlet(s) from the confined space.

Accordingly, the balloon 121 is inflated as follows. The inflation medium is injected into the lumen 143 of the inflation plunger 140. The inflation medium flows distally in the lumen 143 of the inflation plunger 140 and exits the inflation plunger 140 via the one or more apertures 144 to enter the confined space. The inflation medium exits the confined space via the one or more apertures 127 of the balloon shaft 123, passes through the one or more one-way valves 129, and enters the interior of the balloon 121. This completes step 250 of the balloon kyphoplasty procedure 200 illustrated in FIG. 4.

In step 260 of the balloon kyphoplasty procedure 200 illustrated in FIG. 4, the inflation plunger 140 is retracted out of the lumens of the balloon shaft 123 and the balloon member delivery shaft 124. The lumens of the balloon shaft 123 and the balloon member delivery shaft 124 (which together comprise the lumen of the balloon device 120) become unobstructed when the inflation plunger 140 is retracted.

Figure 12:
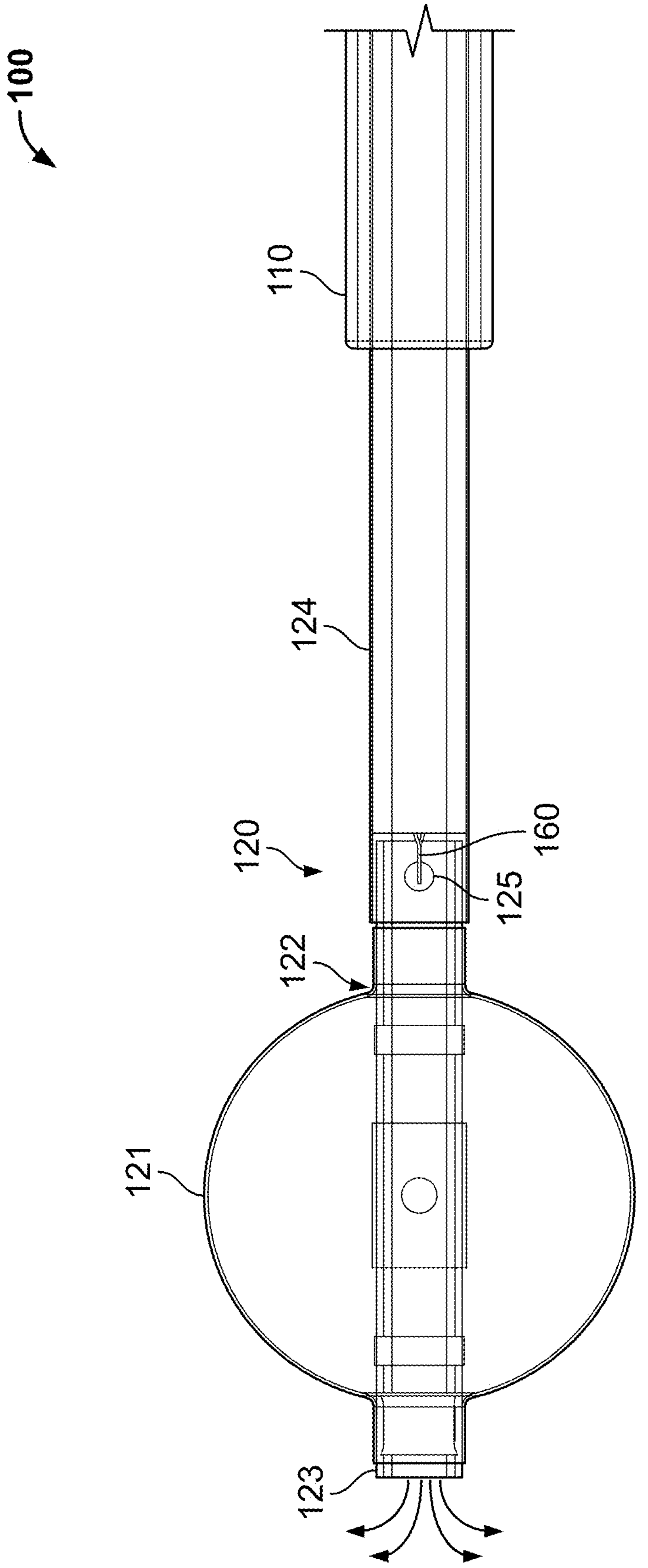
FIG. 12 illustrates a distal portion of an example kyphoplasty system being used to deliver vertebral body filler material.

Still referring to FIG. 4, in step 270 of the balloon kyphoplasty procedure 200 filler material (e.g., orthopedic cement as described above) is injected into the vertebral body cavity through the lumen of the balloon device 120. For example, as depicted in FIG. 12, in some embodiments the distal end of the balloon shaft 123 is open and the filler material can exit the lumen of the balloon device 120 therefrom. Upon exiting the lumen of the balloon device 120, the filler material enters the vertebral body cavity 12, exterior to the balloon 121 (e.g., as depicted in FIG. 3 in comparison to FIG. 2).

In some cases, the performance of step 270 includes the use of an elongate needle (e.g., a 13 gauge needle) to inject the filler material. That is, an elongate needle can be advanced into the lumen of the balloon device 120 and then the filler material can be ejected from the needle such that the filler material enters the vertebral body cavity 12, exterior to the balloon 121.

In step 280 of the balloon kyphoplasty procedure 200, the balloon member delivery shaft 124 is detached from the balloon implant member 122. Thereafter, the balloon member delivery shaft 124 is retracted from the patient while the balloon implant member 122 remains implanted in the vertebral body cavity 12 (e.g., as depicted in FIG. 3).

Various kinds of selectively releasable mechanisms can be used to facilitate the detachment of the balloon member delivery shaft 124 from the balloon implant member 122. For example, in some embodiments a snap fit connection, a threaded connection, a collet mechanism, a bayonet-style connection, and the like, can be used, without limitation. In some embodiments, the balloon member delivery shaft 124 is releasably attached to the balloon implant member 122 by one or more removable sutures 160 as depicted in FIGS. 6 and 12.

Figure 13:
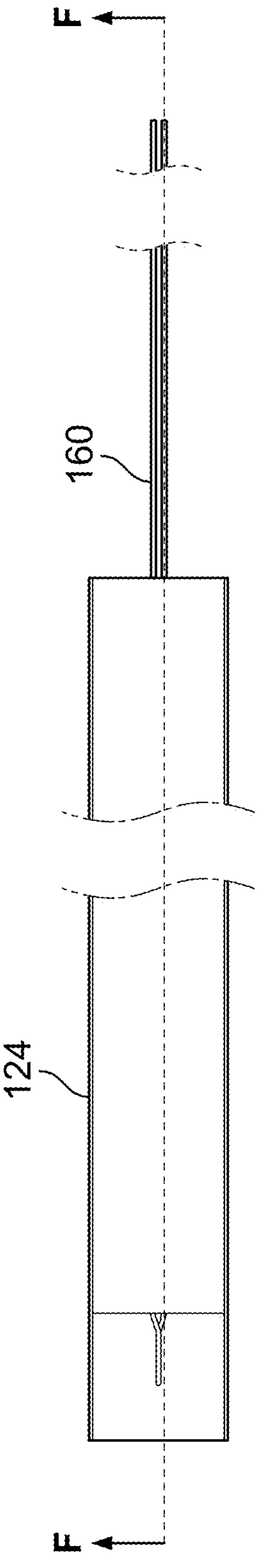
FIG. 13 illustrates an example balloon implant delivery shaft in accordance with some embodiments.
Figure 14:
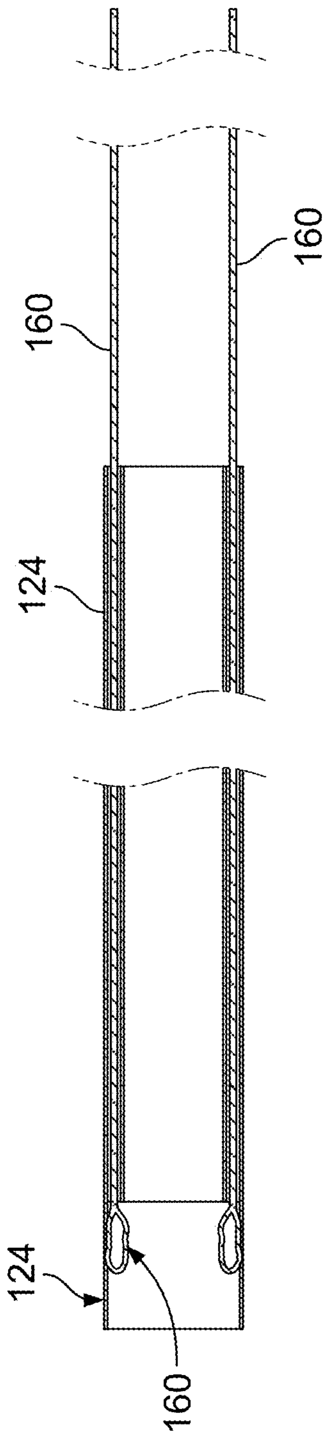
FIG. 14 is a longitudinal cross-section view of the balloon implant delivery shaft of FIG. 13.

As shown in FIGS. 13 and 14, in some embodiments one or more removable sutures 160 (e.g., Kevlar® sutures) can extend through one or more lumens defined within the wall thickness of the balloon member delivery shaft 124. In the depicted embodiment, two removable sutures 160 are included. The two removable sutures 160 form loops at the distal end portion of the balloon member delivery shaft 124, and the two free ends of the two removable sutures 160 are accessible to the practitioner P (FIG. 1) at the proximal end of the kyphoplasty system 100.

Figure 15:
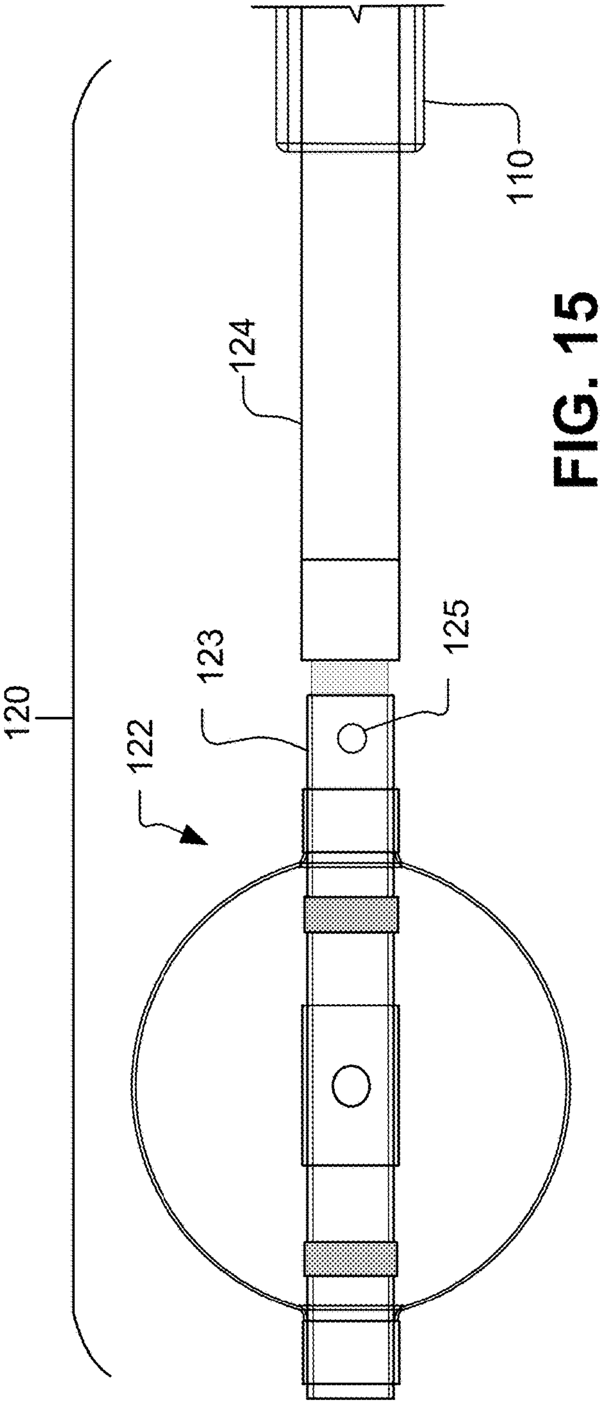
FIG. 15 illustrates the detachment of a balloon implant member from its delivery shaft.
Figure 16:
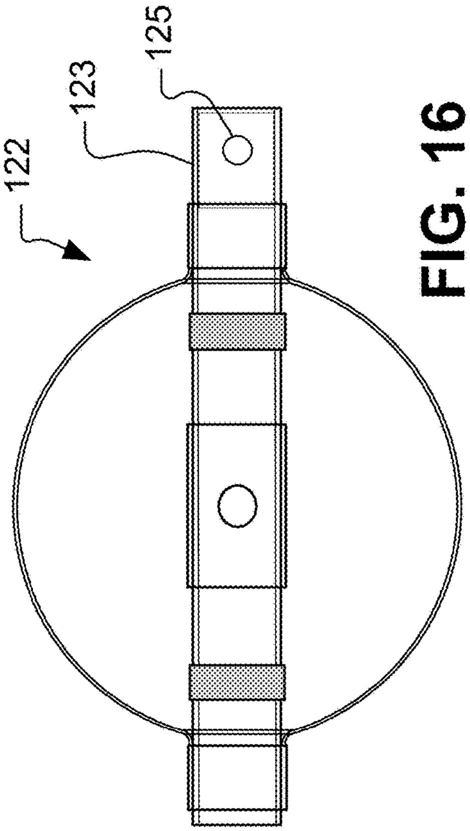
FIG. 16 illustrates the balloon implant member of FIG. 15 in isolation after detachment from its delivery shaft.

Also referring to FIGS. 15 and 16, the balloon shaft 123 can define one or more suture attachment features 125 by which the removable sutures 160 can be attached to the balloon implant member 122. In the depicted embodiment, the one or more suture attachment features 125 are two openings in the balloon shaft 123. The removable sutures 160 can be threaded through (looped through) the two openings in the balloon shaft 123.

In the depicted embodiment, a proximal end portion of the balloon shaft 123 (a portion that includes the two openings 125) extends into a counter-bore at the distal end of the balloon member delivery shaft 124 (where the loops of the two removable sutures 160 reside). The loops of the two removable sutures 160 can pass through the two openings 125 in the balloon shaft 123. Then, when the practitioner P desires to detach the balloon member delivery shaft 124 from the balloon implant member 122 (as per step 280 of the balloon kyphoplasty procedure 200), the practitioner P can cut the two removable sutures 160 at the proximal ends thereof (if necessary) and pull on one free end portion of each of the two removable sutures 160. When a sufficient amount of pulling of the two removable sutures 160 is completed, the two removable sutures 160 will become detached from the suture attachment features 125 (e.g., the two openings 125). Then, as illustrated in FIGS. 15 and 16, the practitioner P can withdraw the balloon member delivery shaft 124 while leaving the balloon implant member 122 implanted in the vertebral body cavity 12 (e.g., as depicted in FIG. 3).

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination.

Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A method for performing a kyphoplasty procedure, the method comprising:

inserting a balloon implant member into a vertebral body, the balloon implant member comprising a balloon configured to expand while in the vertebral body and coaxially mounted on a balloon shaft, wherein the balloon shaft includes one or more inflation ports along a circumferential wall of the balloon shaft to deliver bone cement into an interior of the balloon, wherein the balloon implant member is releasably attached to a distal end portion of a balloon implant detachment shaft such that a detachment shaft lumen defined by the balloon implant detachment shaft and a balloon shaft lumen defined by the balloon shaft adjoin to define a first lumen extending to an open distal end defined by the balloon shaft;

advancing an inflation plunger within the first lumen defined by both the detachment shaft lumen and the balloon shaft lumen to align one or more inflation plunger apertures of the inflation plunger with the one or more inflation ports along the circumferential wall of the balloon shaft;

inflating the balloon by injecting bone cement into a second lumen defined by the inflation plunger that is within the first lumen, where the bone cement is injected through the second lumen and one or more of the inflation apertures to inflate the balloon.

2. The method of claim 1, further comprising:

after inflating the balloon, detaching the balloon implant member from the balloon member detachment shaft such that the balloon implant member remains in the vertebral body.

3. The method of claim 1, further comprising:

after inflating the balloon, injecting filler material into the vertebral body through the first lumen.

4. The method of claim 3, further comprising:

after injecting filler material, withdrawing the balloon member detachment shaft while the balloon implant member remains in the vertebral body.

5. The method of claim 4, wherein the balloon implant detachment shaft is configured to deliver the balloon implant member into the vertebral body while the distal end of the balloon implant detachment shaft is releasably and threadably mated with a proximal end of the balloon shaft.

6. The method of claim 5, further comprising detaching the distal end of the balloon member detachment shaft from the proximal end the balloon shaft both after said inflating the balloon and after said injecting filler material.

7. The method of claim 5, wherein the distal end of the balloon implant detachment shaft is detachable from the proximal end the balloon shaft while the bone cement is arranged in the interior of the balloon of the balloon implant member in the vertebral body.

8. The method of claim 1, wherein each of said one or more inflation ports along the circumferential wall of the balloon shaft includes a one-way valve to seal the bone cement in the interior of the balloon.

9. The method of claim 1, wherein the one or more inflation plunger apertures of the inflation plunger are positioned along an exterior circumferential surface of the inflation plunger that is oriented toward an interior circumferential surface of the circumferential wall of the balloon shaft.

10. The method of claim 1, wherein the inflation plunger is configured to convey the bone cement into the interior of the balloon at a pressure of about 150 psi to about 250 psi.

11. The method of claim 1, wherein the balloon shaft is coaxially aligned and positioned through the interior of the balloon so that the open distal end of the balloon shaft is positioned distally of a distal-most end of the balloon and a proximal end of the balloon shaft is positioned proximally of a proximal-most end the balloon.

12. The method of claim 1, further comprising:

prior to said inserting the balloon implant member into the vertebral body, advancing a bone introducer needle adjacent to the vertebral body; and inserting the balloon implant member into the vertebral body through the bone introducer needle.

13. The method of claim 12, wherein the bone introducer needle is sized to slidably receive the balloon implant member therethrough while the balloon of the balloon implant member is in a collapsed condition.

14. The method of claim 13, wherein an inner portion of the bone introducer needle is removable from an outer portion of the bone introducer needle while a distal end the bone introducer needle is positioned at the vertebral body.

15. The method of claim 14, wherein the balloon implant member is insertable through the outer portion of the bone introducer needle while the balloon implant detachment shaft is releasably and threadably mated with a proximal end of the balloon shaft.

16. The method of claim 1, further comprising:

inserting an elongate needle through the first lumen to deliver bone cement through the open distal end of the balloon shaft and into the vertebral body exterior to the balloon.

17. The method of claim 16, wherein the elongate needle is a 13 gauge needle insertable through the first lumen jointly defined by the balloon shaft and the balloon implant detachment shaft.

18. The method of claim 1, wherein the bone cement comprises at least one of polymethyl methacrylate, calcium phosphate, magnesium phosphate, amorphous magnesium phosphate.

19. The method of claim 1, wherein the inflation plunger comprises at least one seal surface to engage with an interior circumferential surface of the circumferential wall of the balloon shaft.

* * * * *